United States Patent [19]
Nakagawa et al.

[11] Patent Number: 4,749,501
[45] Date of Patent: Jun. 7, 1988

[54] SOLID SOAP COMPOSITION CONTAINING MICROENCAPSULATED HYDROPHOBIC LIQUIDS

[75] Inventors: Yukio Nakagawa; Takayuki Kamura; Hiroto Arai; Masahiro Takizawa; Shoji Konishi, all of Tokyo, Japan

[73] Assignee: Lion Corporation, Tokyo, Japan

[21] Appl. No.: 879,438

[22] Filed: Jun. 27, 1986

[30] Foreign Application Priority Data

Jun. 27, 1985 [JP] Japan .................................. 60-140891
May 14, 1986 [JP] Japan .................................. 61-110257

[51] Int. Cl.$^4$ ..................... C11D 13/00; C11D 17/00
[52] U.S. Cl. ..................................... 252/117; 252/92; 252/132; 252/134; 252/174.13; 252/DIG. 16
[58] Field of Search ............. 252/90, 92, 132, 174.13, 252/134, 108, 117, DIG. 16

[56]  References Cited
U.S. PATENT DOCUMENTS

| 3,043,782 | 7/1962 | Jensen | 427/213.33 |
|---|---|---|---|
| 3,069,370 | 12/1962 | Jensen et al. | 264/4.1 |
| 3,516,937 | 6/1970 | Story et al. | 252/110 |
| 3,705,102 | 12/1972 | Mast | 252/174.13 |
| 3,798,179 | 3/1974 | Hellyer | 252/535 |
| 4,108,600 | 8/1978 | Wong | 8/137 |
| 4,124,521 | 11/1978 | Jedzinak | 252/127 |
| 4,251,386 | 2/1981 | Saeki et al. | 252/316 |
| 4,394,287 | 7/1983 | Scarpelli | 64/4.32 |
| 4,469,613 | 9/1984 | Munteanu et al. | 252/92 |
| 4,597,885 | 7/1986 | Berry et al. | 252/93 |

*Primary Examiner*—Prince E. Willis
*Attorney, Agent, or Firm*—Birch, Stewart, Kolasch & Birch

[57]  ABSTRACT

A solid soap composition comprises a soap base and microcapsules dispersed therein, said microcapsules are prepared by using a hydrophobic liquid as a core material, forming microcapsules by covering the hydrophobic liquid with coacervate of a hydrophilic material, and then adding an electrolyte to a solution having the microcapsules dispersed therein in an amount of 8 to 100 parts by weight to 100 parts by weight of the water used in the microcapsules to dehydrate the microcapsule films. The microcapsules hardly disintegrate during the soap production process but do disintegrate during the use of the soap composition when contacted with water.

9 Claims, No Drawings

SOLID SOAP COMPOSITION CONTAINING MICROENCAPSULATED HYDROPHOBIC LIQUIDS

BACKGROUND OF THE INVENTION

1. Field of the Invention

This invention relates to a solid soap composition containing microcapsules being dispersed therein and, more particularly, to a novel solid soap composition which can be prepared with hardly any disintegration of the microcapsules, the microcapsules being disintegrated only when being used.

2. Description of the Prior Art

Soaps often become discolored and malodor, which results in their degeneration and deterioration, when stored or preserved over a long period of time. Such are caused by phenomena such as oxidation of perfumes, superfatting agents, germicides, and antiphlogistics being added to the soap, or their decomposition and reaction in an alkaline soap. Therefore, the additives which can be added directly to the soap are limited to those which can not cause such degeneration and deterioration, and there were instances in which the desired performance from the soap could not be obtained.

In this case, as a measure to prevent the degeneration and deterioration of a soap due to the addition of such additives, a method to maintain their effects by encapsulating the unstable additives, which are easily degenerated and deteriorated physically or chemically by itself or by reaction with the soap base, may be considered. However, it is rather difficult to make the microcapsules dispersed and contained in the soap without its disintegration occurring during the production of the soap and, at the same time, to allow the core material released by easy disintegration of the microcapsules only in the course of using the soap. Namely, since production of the soap requires processes involving impulse and pressure operation such as kneading, stamping, etc., the microcapsules must be adjusted so as to endure them. On the other hand, the microcapsules must be adjusted at the same time so that they become disintegrated with only a relatively small frictional force in the course of using the soap. Such a microcapsule-containing solid soap satisfying both properties sumiltaneously has not as yet been put into practice.

SUMMARY OF THE INVENTION

The object of this invention is to provide a solid soap composition containing microcapsules which hardly disintegrate during its production, but does disintegrate during its use exhibiting the effects of the core material released from the microcapsules.

As a result of earnest studies concerning a microcapsule-containing solid soap composition in which the microcapsules hardly disintegrates even during the process of the soap production and are disintegrated only during its use to release its contents, the present inventors found that maintaining the property of the impulse and pressure operation in soap production and the property of the microcapsules being capable of being disintegrated by a relatively small frictional force during the use of the soap, are satisfied simultaneously by the use of the microcapsules prepared by using a hydrophobic liquid as the core material, forming microcapsules by covering the hydrophobic liquid with a coacervate of a hydrophilic material, and then adding an electrolyte to a solution having the microcapsules dispersed therein in an amount of 8 to 100 parts by weight to 100 parts by weight of the water used in forming the microcapsules to dehydrate the microcapsule films.

Accordingly, this invention provides a solid soap composition comprising a soap base and microcapsules dispersed therein, said microcapsules are prepared by using a hydrophobic liquid as the core material, forming microcapsules by covering the hydrophobic liquid with a coacervate of a hydrophilic material, and then adding an electrolyte to a solution having the microcapsules dispersed therein in an amount of 8 to 100 parts by weight to 100 parts by weight of the water used in forming the microcapsules to dehydrate the microcapsule films.

According to this invention, since the microcapsules are preserved in the soap until the soap is used, the additives which are physically and chemically unstable neither by itself nor by a reaction with the soap base, can be preserved by encapsulation until the soap is used, so that the effects of the additives such as pharmacological actions, e.g., germicidal and antiphologistic actions, fragrance, beauty acceleration, improvement in appearance of soap, and the like can be exhibited.

According to a preferred embodiment of this invention, the microcapsules, mixed in the soap composition may have a crushing strength of more than 6 $kg/cm^2$ and, more preferably, a particle size of less than 300 $\mu m$, are used in an amount of less than 10% by weight of the composition. The microcapsules having the above-defined crushing strength and the particle size can be suitably blended to the soap composition, as the capsule films hardly disintegrate during the process of the soap production but easily becomes disintegrated during the use of the soap composition which causes a release of the core material.

The above and other objects, features and advantages of this invention will be more apparent from the following descriptions.

DETAILED DESCRIPTION OF THE INVENTION

The soap composition of this invention contains microcapsules being despersed therein. In this invention, the microcapsules used are those prepared by using a hydrophobic liquid as a core material, forming microcapsules by covering the hydrophobic liquid with a coacervate of a hydrophilic material, and then adding an electrolyte to a solution having the microcapsules dispersed therein in an amount of 8 to 100 parts by weight to 100 parts by weight of the water used in forming the microcapsules to dehydrate the microcapsule films, and thereafter drying them. In the microcapsules obtained in this dehydration process, the disintegration of the microcapsules is prevented when they are mixed in the soap composition, and the capsule films are easily dissolved to disintegrate the microcapsules only when contacted with water, causing a release of the core material.

More detailedly, in preparation of the microcapsules using gelatin as the capsule film according to the complex coacervation process, when the capsule film is treated with a hardener such as an aldehyde after covering to insolubilize the gelatin in the capsule film, the capsule film is not dissolved by contact with water, and the core material is released only by disintegration of the capsule film mainly by mechanical force, so that the release control or release efficiency of the core material often becomes ineffective during its use in water-diluted systems. On the other hand, if the capsule film had not been subjected to the hardening treatment and also had not been subjected to the dehydration treatment after covering the core material by means of the complex coacervation process, the capsule film would become more than the gel point when the microcapsule in equilibrium to the capsule-dispersed solution is separated and washed as it is, and not only would it shortly become dissolved to release the core material, but also the drying efficiency becomes ineffective, because disintegration is caused during the drying process. Accordingly, although the dehydration of the capsule film, when the hardening treatment is not carried out after covering in the complex coacervation, is an important process in increasing the productive efficiency of the microcapsules, a preferable treatment method has so far not been obtained.

However, as stated above, the treatment of the microcapsules obtained by the coacervation process with an electrolyte in an amount of 8 to 100 parts by weight to 100 parts by weight of the water used in forming the microcapsules is very effective as a dehydration process of the capsule films without hardening treatment. In the microcapsules obtained by adding the electrolyte to the solution having the microcapsules dispersed therein in the above used amount, the capsule films are certainly dehydrated and the drying efficiency is excellent when the microcapsules are dried. Additionally, the films thus dehydrated or dried after dehydration are stable, hardly disintegrated when mixed with the soap composition, and stably stored in the soap composition without releasing the core material over a long period and, further, since the microcapsules are not subjected to hardening treatment, they are easily disintegrated to release the core material when the soap composition is contacted with water. The dehydration process is further illustrated in more detail.

The process comprises using a hydrophobic liquid as the core material, covering this hydrophobic liquid with a coacervate of hydrophilic colloid to form microcapsules, then adding an electrolyte to the solution having the microcapsules dispersed therein to dehydrate the microcapsule films. As the process for preparing the microcapsules, the coacervation process, particularly the complex coacervation process, is preferably used.

The hydrophilic colloid preferably comprises an aqueous solution containing gelatin and an anionic hydrophilic high molecular substance. In this case, the microcapsules can preferably be prepared by dispersing the hydrophobic core material in the aqueous solution of gelatin, mixing it with an aqueous solution of anionic hydrophilic high molecular substance, and adjusting to the optimum pH. The total concentration of gelatin and the anionic hydrophilic high molecular substance in the solution is preferably 10% by weight or less, and the temperature is properly selected according to the conventional method, but the hydrophobic core material is preferably dispersed with maintaining 35° to 45° C.

The anionic hydrophilic high molecular substance is suitably selected according to the purposes, and those used in preparation of general microcapsules can be used. For example, gum arabic, alkali metal salt of carboxymethyl cellulose, sodium alginate, carrageenan, maleic acid derivatives (styrene-maleic anhydride copolymer, methyl vinyl ether-maleic anhydride copolymer, etc.), acrylic acid copolymer, polyvinylbenzene sulfonic acid, carboxymethyl starch and the like are preferably used, and they may be used alone or in combination of two or more of them.

The addition amount of the anionic hydrophilic high molecular substance is not particularly limited, and the general use range can be used. The preferable weight ratio of the anionic hydrophilic high molecular substance to gelatin is 0.9 to 1.1 for gum arabic and 0.3 to 0.5 for sodium carboxymethyl cellulose, The core material (hydrophobic liquid) to be encapsuled in the microcapsules include various materials, and various kinds of additives are used in relation to the demand to the compositions. In general, expensive additives of a small amount and physically and chemically unstable additives are effectively used, and the examples include perfumes, germicides, antiphologistics, moisture-holding agents, vitaminins and the like. Also, various oils such as natural mineral oil, natural animal oil, natural vegetable oil, and synthetic oil, including paraffin oil, fish oil, beef tallow, olive oil, corn oil, rind oil, alkylated naphthalene, alkylated biphenyl, silicone oil, etc., can be used. These materials may be used alone or in combination of two or more of them. In order to increase the beauty of the product, the microcapules used in this invention also may contain a coloring agent such as coloring matters and pigments or a pearl agent such as titanium mica and scale leaf in the core material or the wall material.

After covering the surface of the core material with the hydrophilic colloid (the coacervate) of an aqueous solution of gelatin and anionic hydrophilic high molecular substance, it is preferred to gel the gelatin sufficiently, simultaneously with improving the encapsulation. The treatment conditions of this case are not particlularly limited, but a suitable acceleration of the encapsulation and also gelation of the gelatin can be achieved by adjusting the pH of the liquid to 3 to 4.5 using an acid including inorganic acids such as hydrochloric acid and sulfuric acid and organic acids such as acetic acid and citric acid, and cooling the temperature of the liquid gradually to the gel temperature of gelatin or less, preferably 35° C. to 0° C., more preferably 15° C. or less.

Next, after covering the core material, the sufficiently gelled capsule films are preferably dehydrated using an electrolyte, and further dried to prepare water-soluble gelatin film capsules in which the capsule films are easily dissolved when contacted with water to release the core material, exhibiting its effect.

The electrolyte is selected in consideration of the preservation method of the capsules and the influence on the product to be mixed, but water-soluble inorganic compounds or organic compounds having a high solubility to water are preferably used in the form of salt or acid. For example, as the electrolyte, sulfuric acid, sulfurous acid, hydrochloric acid, phosphoric acid, methaphosphoric acid, boric acid, carbonic acid, iodic acid, nitric acid, nitrous acid, citric acid, tartaric acid, acetic acid, or alkali metal salts or ammonium salts thereof are preferably used, and amino acids such as glycine, alanine, glutamic acid and the like as well as their salts may be also used. Among them, the electrolytes which have a sufficient solubility at the above gel temperature of the gelatin film or less and can maintain the microcapsule-dispersed solution in the range of pH 3 to 4.5 are preferable to accelerate encapsulation, for example, sodium sulfate, sodium dihydrogenphosphate, and sodium chloride are preferably used, and the dehydration treatment can be easily achieved by using them.

The amount of the electrolyte is selected depending on the kind, but the high concentration is preferred to improve further the dehydration of the capsule-containing water, and an excellent dehydration treatment can be achieved by using 8 to 100 parts by weight, more preferably 15 to 70 parts by weight to 100 parts by weight of the water used in forming the capsules.

The addition method is not particularly limited, but the electrolyte is preferably added after sufficient gelation of the gelatin film of the capsules, as mentioned above. The electrolyte may be added and mixed in the capsule-dipersed solution as an aqueous solution, or directly added thereto, but in both cases, the electrolyte is preferably added gradually with sufficiently stirring the capsule-dispersed solution. Further, when the solubility of the electrolyte is low, the objective dehydration condition can be achieved by conducting a primary dehydration by using a little amount of the electrolyte having a low solubility, increasing the temperature of the capsule-dispersed solution with observing the condition of the capsule film to increase the solubility of the electrolyte, then conducting the dehydration treatment again by adding the residual amount of the electrolyte.

The preservation of the capsules thus dehydrated by the electrolyte treatment is not particularly limited, but the capsules are preferably washed with the same electrolyte (preferably the same kind and same concentration) as the electrolyte treatment, separated, and then preserved in the same aqueous solution of the electrolyte. According to the uses, it may be filtered, dried in the air, and pulverized. Also, in order to prevent cohesion of the capsules each other in drying and pulverization, a process of adding and dispersing homogeneously a fine solid, for example, tark, etc, followed by drying and pulverization may also be preferably adapted.

As the microcapsules, those having a crushing strength of more than 6 kg/cm$^2$, preferably more than 8 kg/cm$^2$ are suitable, and the use of this kind of microcapsules enables to obtain the microcapsule-containing soap composition in which the microcapsules are not disintegrated in soap production. When the strength of the microcapsules is smaller than 6 kg/cm$^2$, the greater part of the microcapsules may be crushed by a mechanical force during soap production.

The particle size of the microcapsules used in this invention is suitably less than 300 μm, more preferably less than 200 μm. At beyond 300 μm, most of the microcapsules may be disintegrated with the mechanical strength of soap production.

The blending amount of the microcapsules in the soap composition is suitably less than 10% by weight. At beyond 10%, a decrease in lathering and cracks are caused in the soap composition to reduce the performance thereof, which become a problem in commercial value. The blending amount of the microcapsules is more preferably less than 6%.

The soap composition of this invention comprises dispersing the microcapsules as described above in the soap base homogeneously. The soap base can be prepared according to conventionally known processes. For example, it can be prepared by saponifying each or a mixture of animal oils including beef tallow, lard, whale oil and fish oil and vegetable oils including coconut oil, palm oil, palmkernel oil, soy-bean oil, olive oil, and cottonseed oil with alkali, or neutralizing various fatty acids and resin acids with alkali.

This soap base may contain various components as well as the microcapsule. These components include perfumes, stabilizers such as EDTA, EHDP or alkali metal salts thereof. Other surfactants may be added to the composition of this invention to improve the washing power furthermore. The examples of the surfactant include α-sulfo fatty acid ester, isetionic acid ester, alkyl arylsulfonic acid, alcohol sulfuric acid ester, sulfuric acid ester of alcohol ethoxylate, olefinsulfonic acid, parasulfonic acid, N-acylglutamic acid and salt of these esters and acids, as well as alkyl betaine and alkylsulfobetaine.

To control the residual oil effect on the skin, superfatting agent and various skin protective agent may be added. The examples thereof include hydrocarbons such saqualene, squalane, olefin oligomer, wax, vaseline and other mineral oils, fatty acids such as stearic acid, isostearic acid, oleinic acid, ricinolic acid, palmitic acid, myristic acid, behenic acid and the like, fatty acid esters such as various glycerides, sugar esters, lanoline, isopropyl myristate, isopropyl palmytate, isobutyl stearate and the like, aliphatic alcohols such as cetyl alcohol, stearyl alcohol, oleyl alcohol and the like, polyols such as glycerol, polyethylene glycol, polypropylene glycol and the like, ethoxylates of alcohol and fatty acid, silicones such as dimethyl silicone and the like, various proteins and protein derivatives, and vitamins. Furthermore, the soap composition of this invention may contain coloring matters, antiphlogistics such as alantoin and dipotassium glythyrrhizinate, and germicides such as 2,4,4'-trichloro-2'-hydroxydiphenyl ether and 3,4,4'-trichlorocarbanilide (TCC). Though these may be used as the core material of the microcapsules, they may be added to the soap base separately, simultaneously with adding in the microcapsules.

As a method to prepare the soap composition using the above components, any known method can be employed, and a method of mixing the microcapsules and other necessary components with the soap base homogeneously by means of a mixer and extruding it using a roll or prodder, followed by stamping is generally adapted.

Since the microcapsules are not disintegrated in production of the soap composition and is disintegrated in using the soap composition because of the use of the microcapsules prepared by a specific method including the electrolyte treatment mentioned above, the soap composition of this invention can maintain the properties of various soap additives till using the soap composition by encapsulizing them, resulting in effective exhibition of the properties of the encapsulized additives. Further, the soap composition of this invention not only does not show reduction of the washing power and other soap performance at all even when stored or preserved for a long time, but also has a remarkably improved satisfactory stability without inconvenient phenomena such as discoloration and change of smell, and thus is excellent in commercial value and practical value.

This invention is further illustrated by Examples and Comparative Examples, but this invention is not limited by the following Examples.

EXAMPLES 1 AND 2, COMPARATIVE EXAMPLE 1

In a beaker having a volume of 1 liter with a stirrer, 160 g of an aqueous solution of 10% gelatin were dissolved in 480 g of distilled water, and 40 g of floral type flavor was added thereto and dispersed so as to form oil drop having a predetermined average particle size with maintaining the temperature of the mixture at 45° C. Then, 160 g of an aqueous solution of 10% gum arabic was added and mixed therein. The reaction mixture was adjusted to pH 4.2 using acetic acid to deposit the coacervate around the oil drop of the flavor. Further, the temperature of the mixture was gradually cooled to 15° C. to gel the capsule film sufficiently.

Next, to this capsule-dispersed solution, 115 g of sodium sulfate (15 parts by weight to 100 parts by weight of the water used in forming the capsules) as an electrolyte was slowly added under stirring for dehydration. In this case, it was observed by microscope that the water-containing gelling film of gelatin/gum arabic was dehydrated to form a strong film. As no cohesion between the capsules was observed, the capsules were washed with an aqueous solution of 15% sodium sulfate, separated, and then dried to pulverize.

The thus obtained dry pulverized microcapsules were added to a hot water at 30° C. At a result, it was observed that the capsule films were shortly swelled and dissolved to emit the fragrance of floral type flavor, and the release of the flavor which was the core material, was confirmed.

Next, 2% by weight of the microcapsules obtained by the above method was added to 98% by weight of the soap base (a sodium soap obtained from a oil having a weight ratio of beef tallow/coconut oil=80/20, water content 10%) and mixed homogeneously by means of a mixer, then the soap was extruded by a prodder, followed by stamping to afford a soap composition containing the microcapsules homogeneously dispersed in the base.

EXAMPLE 3, COMPARATIVE EXAMPLE 2

Using as the core material 40 g (for Example 3) or 70 g (for comparative Example 2) of the mixture of oily vitamin and liquid paraffin in a weight ratio of 1:10, microcapsules prepared and dehydrated in the same manner as in Examples 1 and 2 were washed, separated and preserved in an aqueous solution of 15% sodium sulfate.

When the microcapsules were filtered, separated, dried, pulverized and added to a hot water at 30° C., the capsule films were shortly swelled and dissolved, and the release of the core material was confirmed.

Also, when the pulverized capsules were allowed to stand at 45° C. for 2 months, the reduction of the capsule weight was only 0.5% by weight, and it was confirmed that the capsules were excellently elaborate.

Next, 70 g of a soap base (a sodium soap obtained from an oil having a ratio of palm oil/coconut oil/castor oil=70/20/10), 28 g of sodium isetionate, 0.25 g of titanium oxide, and 1.75 g of the microcapsules prepared as above were mixed and stamped to prepare a soap composition in the same manner as in Examples 1 and 2.

EXAMPLE 4, COMPARATIVE EXAMPLES 3 AND 4

Using 25 g of α-pinene as the core material, microcapsules prepared and dehydrated in the same manner as in Examples 1 and 2 by adding 230 g of sodium citrate (30 parts by weight to 100 parts by weight of the water used in forming capsules) as an electrolyte were washed, separated and then preserved in an aqueous solution of 23% sodium citrate.

The capsules were evaluated on the releasing property in the same manner as in Examples 1 and 2. As a result, it was confirmed that α-pinene which was the core material was easily released in a hot water at 30° C.

For comparison, the same procedure as above was repeated except that the dehydrating treatment was omitted or a hardening treatment by using formaldehyde was conducted instead of the dehydrating treatment.

The thus obtained microcapsules were evaluated on the releasing property. As a result, the microcapsules obtained by omitting the dehydrating treatment (Comparative Example 3) easily released their core material (α-pinene). On the other hand, the release of the core material (α-pinene) was not observed in the microcapsules obtained by conducting the hardening treatment (Comparative Example 4).

Next, the soap compositions in which the above microcapsules were dispersed were pepared in the same manner as Examples 1 and 2.

EXAMPLES 5 AND 6, COMPARATIVE EXAMPLE 5

In a beaker having a volume of 1 liter with a stirrer, 170 g of an aqueous solution of 10% gelatin were dissolved in 490 g of distilled water, and 40 g of a mixed oil consisting of 10 g of squalene, 20 g of olive oil and 10 g of lemon oil were added and dispersed therein to adjust the particle size. Then, 140 g of an aqueous solution of 5% sodium carboxymethyl cellulose were added and mixed. This mixture was adjusted to pH 3.9 using acetic acid to deposit the coacervate around the oil drop of the mixed oil. Further, the temperature of the mixture was gradually cooled to 15° C. to gel the capsule films sufficiently.

The microcapsules were dehydrated in the same manner as in Examples 1 and 2 by adding 194 g of sodium chloride (25 parts by weight to 100 parts by weight of the water used in forming the capsule) as an electrolyte for dehydration, washed, separated and preserved in an aqueous solution of 20% sodium chloride.

When the capsules were filtered, seperated and added to a hot water at 30° C., the capsule films were shortly swelled and dissolved, and the fragrance of lemon oil was emitted and the core material was confirmed to be released.

Next, the soap compositions in which the above microcapsules were dispersed were prepared in the same manner as in Example 3.

EXAMPLE 7

Using the same mixed oil as in Examples 5 and 6 as the core material, microcapsules were prepared in the same manner as in Example 5 and the temperature of the reaction mixture was gradually cooled to 15° C. to gel the capsule films sufficiently.

Then the capsules were added to 800 g of an aqueous solution of 25% sodium dihydrogenphosphate (containing 26 parts by weight of sodium dihydrogenphosphate to 100 parts by weight of the water used in forming the capsules) under stirring and disperesed tehrein. After sufficient stirring, the capsules were separated. Then washing with an aqueous solution of 25% sodium dihydrogenphosphate at 15° C. and separation were repeated three times and the separated capsules were dispersed in an aqueous solution of 25% sodium dihydrogenphosphate and preserved therein.

When the capsules were filtered, separated and added to hot water at 30° C., the capsule films were shortly swelled and dissolved and the release of the core material was confirmed.

Next, the soap composition in which the above microcapsules were dispersed was prepared in the same manner as in Examples 1 and 2.

The materials used for preparation of the microcapsules in the above Examples 1 to 7 and Comparative Examples 1 to 5 and the final forms of the microcapsules are summarized in Table 1.

Table 1 shows the average particle sizes and the crushing strengths of the microcapsules as well as the properties of the soap compositions.

The crushing strength of the microcapsules was measured as follows.

A part of the microcapsules obtained by the above method was placed in a separate small glass plate. Using a rheometer (manufactured by Fudo Industry Co., Ltd., NRM-2002J), an adaptor on a cylinder having a diameter of 2.9 mm with a flat bottom was set up and the external pressure was given to the microcapsules using the adaptor. The external pressure at that time was read, and at the same time, the numbers of the microcapsules disintegrated by the given external pressure and the remaining microcapsules were measured by microscopic observation.

The properties of the soap composition were evaluated as follows.

The number of the microcapsules remaining after production of the microcapsule-containing soap composition and the number of the microcapsules remaining in the washing solution after washing with this soap composition were counted and compared with the number of the added microcapsules.

For the number of the microcapsules in the soap composition, a fixed amount of the soap was taken in a beaker, and about 30 time amount of water was added thereto, dissolving the soap composition at 15° C. This solution was centrifugated at 1000 r.p.m. for 5 minutes and the microcapsules were taken out. After they were further diluted with 25 time amount of distilled water (about 15° C.), a fixed amount was taken out and the number of the microcapsules was measured by microscope. The washing method of soap composition was the same as the general usage, and the soap composition was scrubbed with tap water and its washing solution was collected. For the number of the microcapsule remaining in the obtained washing solution, the solution was centrifugated in the same manner as described above, and the number of the microcapsules was measured by microscope.

The fragrance and stability of each soap composition were evaluated according to the following method and standards.

(1) Emission of fragrance of the soap composition

A sensuous test by the following 4 rank method was carried out by 50 persons and evaluated by the average.
  4: Emission of fragrance when the core material kneaded in the soap composition without capsulization.
  3: Slightly weaker than 4.
  2: Weaker than 4.
  1: Much weaker than 4.

(2) Emission of fragrance in using

A sensuous test by the following 4 rank method was carried out by 50 persons and evaluated by the avarage.
  4: Emission of fragrance when used after the soap composition in which the core material was kneaded without capsulization was sealed and preserved in a cool dark place for 2 months.
  3: Slightly weaker than 4.
  2: Weaker than 4.
  1: Much weaker than 4.

(3) Evaluation of color tone stability

A macroscopic evaluation by the following 4 rank method was carried out by 50 persons.
  0: No difference, compared with the control sample preserved in a cool dark place.
  1: Slightly discolored, compared with the control sample preserved in a cool dark place.
  2: A little discolored, compared with the control sample preserved in a cool dark place.
  3: Fairly discolored, compared with the control sample preserved in a cool dark place.

| | Example 1 | Example 2 | Comparative Example 1 |
|---|---|---|---|
| Core material | Floral type flavor | Floral type flavor | Floral type flavor |
| Anionic hydrophilic high molecular substance | Gum arabic | Gum arabic | Gum arabic |
| Electrolyte for hydration Compound Addition amount* | $Na_2SO_4$ 15 | $Na_2SO_4$ 15 | $Na_2SO_4$ 15 |
| Final form of microcapsules | Pulverized | Pulverized | Pulverized |
| Average particle size of microcapsules ($\mu$m) | 150 | 70 | 350 |
| Crushing strength of microcapsules (kg/cm$^2$) | 10 | 15 | 10 |
| Capsule crushing ratio in production (%) | 37 | 15 | 66 |
| Capsule releasing ratio upon use (%) | 60 | 81 | 33 |
| Capsule remaining ratio (%) | 3 | 4 | 1 |
| Emission of fragrance of product | 2.4 | 1.8 | 3.0 |
| Emission of fragrance upon use | 3.2 | 3.8 | 2.1 |
| Color tone after storage | 1 | 0 | 3 |

Note
*Weight parts to 100 weight parts of the water used in forming the capsules

| | Example 3 | Comparative Example 2 |
|---|---|---|
| Core material | Oily vitamine + liquid paraffin | Oily vitamin + liquid paraffin |
| Anionic hydrophilic high molecular substance | Gum arabic | Gum arabic |
| Electrolyte for hydration Compound Addition amount* | $Na_2SO_4$ 15 | $Na_2SO_4$ 15 |
| Final form of microcapsules | Pulverized | Pulverized |
| Average particle size of microcapsules ($\mu$m) | 40 | 150 |
| Crushing strength of microcapsules (kg/cm$^2$) | 20 | 4 |
| Capsule crushing ratio in production (%) | 6 | 70 |
| Capsule releasing ratio upon use (%) | 90 | 29 |
| Capsule remaining ratio (%) | 4 | 1 |
| Emission of fragrance | — | — |

|  | Example 3 | Comparative Example 2 |
|---|---|---|
| of product |  |  |
| Emission of fragrance upon use | — | — |
| Color tone after storage | 1 | 4 |

Note
*Weight parts to 100 weight parts of the water used in forming the capsules

|  | Example 4 | Comparative Example 3 | Comparative Example 4 |
|---|---|---|---|
| Core material | α-pinene | α-pinene | α-pinene |
| Anionic hydrophilic high molecular substance | Gum arabic | Gum arabic | Gum arabic |
| Electrolyte for hydration Compound Addition amount* | Sodium citrate 30 | — | Hardening treatment |
| Final form of microcapsules | Dispersed in 23% sodium citrate aqsolution | Dispersed in 23% sodium citrate aqsolution | Dispersed in water |
| Average particle size of microcapsules (μm) | 10 | 20 | 20 |
| Crushing strength of microcapsules (kg/cm$^2$) | 28 | 2 | 15 |
| Capsule crushing ratio in production (%) | 4 | 96 | 48 |
| Capsule releasing ratio upon use (%) | 95 | 4 | 2 |
| Capsule remaining ratio (%) | 1 | 0 | 50 |
| Emission of fragrance of product | 1.3 | 3.8 | 2.7 |
| Emission of fragrance upon use | 4.0 | 1.4 | 1.1 |
| Color tone after storage | 0 | 2 | 2 |

Note
*Weight parts to 100 weight parts of the water used in forming the capsules

EXAMPLE 8, COMPARATIVE EXAMPLE 6

Using the microcapsules prepared in the same manner as in Example 3, the soap composition having the following formulation were prepared.

|  | Example 8 | Comparative Example 6 |
|---|---|---|
| POE (15 mol) methyl glucoside ether | 0.3% | 0.3% |
| Cetanol | 4.8 | 4.8 |
| Sodium stearoyl-L-glutamate | 73.3 | 69.8 |
| Microcapsules | 8.6 | 12.0 |
| Perfume | 1.0 | 1.0 |
| Deionized water | Balance | Balance |
|  | 100.0% | 100.0% |

The soap composition of Example 8 had good performance. On the other hand, the soap composition of Comparative Example 6 had poor lathering and caused cracks therein.

What is claimed is:

1. A solid soap composition comprising a soap base having microcapsules dispersed therein, said microcapsules having been prepared by: encapsulating, in an aqueous medium, a hydrophobic liquid core material with a hydrophilic coacervate of hydrophilic colloid comprising an aqueous solution containing gelatin and an anionic hydrophilic high molecular substance; adjusting the pH of the aqueous solution to form a capsule film; cooling the temperature of the aqueous solution to the gel temperature of gelatin or less, and: adding to said aqueous solution at least one electrolyte selected from the group consisting of alkali metal salts and ammonium salts of sulfuric acid, sulfurous acid, hydrochloric acid, phosphoric acid, methaphoric acid, boric acid, carbonic acid, iodic acid, nitric acid, nitrous acid, citric acid, tartaric acid, acetic acid and amino acids in an amount of 8 to 100 parts by weight to 100 parts by weight of the water used in forming the dispersed encapsulated product to dehydrate the dispersed encapsulated product and to form the microcapsules.

2. The solid soap composition according to claim 1 wherein the microcapsules have a crushing strength of

|  | Example 5 | Example 6 | Comparative Example 5 | Example 7 |
|---|---|---|---|---|
| Core material | Squalene + Olive oil + lemon oil | Squalene + Olive oil + lemon oil | Squalene + Olive oil + lemon oil | Squalene + Olive oil + lemon oil |
| Anionic hydrophilic high molecular substance | CMC—Na | CMC—Na | CMC—Na | CMC—Na |
| Electrolyte for hydration Compound Addition amount* | NaCl 25 | NaCl 25 | NaCl 25 | NaH$_2$PO$_4$ 26 |
| Final form of microcapsules | Dispersed in 20% NaCl Aqsolution | Dispersed in 20% NaCl Aqsolution | Dispersed in 20% NaCl Aqsolution | Dispersed in 25% NaH$_2$PO$_4$ solution |
| Average particle size of microcapsules (μm) | 100 | 60 | 400 | 200 |
| Crushing strength of microcapsules (kg/cm$^2$) | 17 | 22 | 7 | 13 |
| Capsule crushing ratio in production (%) | 24 | 10 | 74 | 32 |
| Capsule releasing ratio upon use (%) | 73 | 86 | 26 | 65 |
| Capsule remaining ratio (%) | 3 | 4 | 0 | 3 |
| Emission of fragrance of product | 2.0 | 1.6 | 3.4 | 2.3 |
| Emission of fragrance upon use | 3.5 | 4.0 | 2.0 | 3.2 |
| Color tone after storage | 1 | 1 | 3 | 1 |

Note
*Weight parts to 100 weight parts of the water used in forming the capsules more than 6 kg/cm² and are dispersed in an amount of 10% by weight of the total weight of the composition.

3. The solid soap composition according to claim 1 wherein the particle size of the microcapsules is less than 300 μm.

4. The solid soap composition according to claim 1 wherein the hydrophilic colloid comprises an aqueous solution containing gelatin and an anionic hydrophilic high molecular substance.

5. The solid soap composition according to claim 1 wherein said hydrophilic coacervate is an anionic hydrophilic high molecular weight substance is gum arabic, alkali metal salt of carboxymethyl cellulose, sodium alginate, carrageenan, styrene-maleic anhydride copolymer, methyl vinyl ether-maleic anhydride copolymer, acrylic acid copolymer, polyvinylbenzene sulfonic acid, carboxymethyl starch or mixtures thereof.

6. The solid soap composition according to claim 1 wherein the hydrophobic liquid core material is perfumes, germicides, antiphlogistics, moisture-holding agents, vitamins, natural mineral oil, natural animal oil, natural vegetable oil, paraffin oil, fish oil, beef tallow, olive oil, corn oil, rind oil, alkylated naphthalene, alkylated biphenyl, silicone oil, a coloring agent or mixtures thereof.

7. A process for producing a solid soap composition which comprises a soap base having microcapsules dispersed therein; said process comprising: encapsulating, in an aqueous medium, a hydrophobic liquid core material with a hydrophilic coacervate of hydrophilic colloid comprising an aqueous solution containing gelatin and an anionic hydrophilic high molecular substance; adjusting the pH of the aqueous solution to form a capsule film; cooling the temperature of the aqueous solution to the gel temperature of gelatin or less, and: adding to said aqueous solution at least one electrolyte selected from the group consisting of alkali metal salts and ammonium salts of sulfuric acid, sulfurous acid, hydrochloric acid, phosphoric acid, methaphoric acid, boric acid, carbonic acid, iodic acid, nitric acid, nitrous acid, citric acid, tartaric acid, acetic acid and amino acids in an amount of 8 to 100 parts by weight to 100 parts by weight of the water used in forming the dispersed encapsulated product to dehydrate the dispersed encapsulated product and to form the microcapsules; dispersing the microcapsules in a soap base to form a solid soap composition.

8. The process according to claim 7, wherein the anionic hydrophilic high molecular weight substance is selected from gum arabic, alkali metal salt of carboxymethyl cellulose, sodium alginate, carrageenan, styrene-maleic anhydride copolymer, methyl vinyl ether-maleic anhydride copolymer, acrylic acid copolymer, polyvinylbenzene sulfonic acid, carboxymethyl starch or mixtures thereof.

9. The process according to claim 7, wherein the hydrophobic liquid core material is selected from perfumes, germicides, antiphlogistics, moisture-holding agents, vitamins, natural mineral oil, natural animal oil, natural vegetable oil, paraffin oil, fish oil, beef tallow, olive oil, corn oil, rind oil, alkylated naphthalene, alkylated biphenyl, silicone oil, a coloring agent or mixture thereof.

* * * * *